United States Patent [19]
Goldfarb et al.

[11] Patent Number: 6,013,659
[45] Date of Patent: Jan. 11, 2000

[54] METHODS OF REDUCING TUMOR COLONY NUMBER USING NOVEL BENZOTHIAZOLE COMPOUNDS

[75] Inventors: Ronald H. Goldfarb, Arlington, Tex.; Masami Ohashi, Ibaraki; Kohichiro Yoshino, Suita, both of Japan

[73] Assignee: University of Pittsburgh, Pa.

[21] Appl. No.: 09/148,774

[22] Filed: Sep. 4, 1998

[51] Int. Cl.[7] .......................... A01N 43/78; A61K 31/425
[52] U.S. Cl. .................. 514/367; 424/185.1; 424/184.1; 424/198.1; 424/93.7
[58] Field of Search ............................. 424/185.1, 184.1, 424/198.1, 93.7; 514/367

[56] References Cited

U.S. PATENT DOCUMENTS

| | | |
|---|---|---|
| 3,669,979 | 6/1972 | Freyermuth . |
| 4,556,411 | 12/1985 | Baum et al. . |
| 4,705,861 | 11/1987 | Furstenwerth et al. . |
| 4,910,211 | 3/1990 | Imamura et al. . |
| 5,236,619 | 8/1993 | Iwaki et al. . |

FOREIGN PATENT DOCUMENTS

| | | |
|---|---|---|
| 0 306 708 A1 | 3/1989 | European Pat. Off. . |

OTHER PUBLICATIONS

"Enhanced anti–metastatic efficacy of IL–2 activated NK (A–NK) cells with novel benzothiazoles" R. H. Goldfarb et al, Anticancer Research, submitted, 1998.

"Enhanced anti–metastatic efficancy of IL–2 activated NK (A–NK) cells with novel benzothiazoles", R. H. Goldfarb et al, FASEB J., 12:A475:2763, 1998.

"Preclinical studies of IL–2 activated natural killer effector cells for locoregional therapy of metastatic cancer", R. H. Goldfarb, Journal of Infusional Chemotherapy, 4:77–82, 1994.

"Augmentation of IL–2 activated natural killer cell adoptive immunotherapy with cyclophosphamide", R. H. Goldfarb et al, Anticancer Research, 18:1441–1446, 1998.

"Augmentation of IL–2 natural killer cell adoptive immunotherapy with cyclosphosphamide", R. H. Goldfarb et al, Proceedings of the American Association for Cancer Research Meeting, 37:480, 1996.

"Flavone acetic acid enhances accumulation of IL–2 activated NK cells within established metastases", R. P. Kitson et al, In Vivo, in press, 1998.

Flavone acetic acid enhancement of IL–2 activated NK cell accumulation within established metastases as assessed by quantitative image analysis, R. P. Kitson et al, Proceedings of the American Association for Cancer Research Meeting, 35:480, 1994.

"IL–2 activated NK cells: Interactions with tumor cells and endothelial cells within tumor metastases: Necessary but not sufficient for therapy of established metastases?", R. H. Goldfarb et al, Nat. Immunity, 13:228–229, 1994.

Natural Immunity, 1994:131–140, "Natural Killer Cells and Gene Therapy: Potential of Gene Transfection for Optimizing Effector Cell functions and for Targeting Gene Products into Tumor Metastases".

"Localization of Immune Effector Cells to Tumor Metastases", Ronald H. Goldfarb, Theresa L. Whiteside, Tumor Immunology and Cancer Therapy, 1994, pp. 149–158.

"Accumulation of Adoptively Transferred Adherent, Lymphokine–activated Killer Cells in Murine Metastases",P. Basse, et al., vol. 174, Aug. 1991, 479–488.

Tissue distribution of adoptively transferred adherent lymphokine–activated killer cells assessed by different cell labels, P. Basse, et al., Cancer Immunology Immunotherapy, 1992, 34:221–227.

Establishment of Cell–to–Cell Contact by Adoptively Transferred Adherent Lymphokine–Activated Killer Cells With Metastatic Murine Melanoma Cells, P.Basse et al., Journal of the National Cancer Institute, vol. 83, No. 13, Jul. 3, 1991, pp. 944–950.

"Tissue Distribution of Adoptively Transferred Adherent LAK Cells: Role of the Route of Administration", Natural Immunity, 1992, 11:193–202.

"Accumulation of Adoptively Transferred A–NK Cells in Murine Metastases: Kinetics and Role of Interleukin–2", P.H. Basse et al., in vivo, 8:17–24 (1994).

"Novel Disease–Modifying Antirheumatic Drugs. I. Synthesis and Antiarthritic Activity of 2–(4–Methylphenyl)benzothiazoles", Hori et al., Chem. Pharm. Bull. 40(9), pp. 2387–2390 (1992).

"Structural Studies on Bioactive compounds, 23, Synthesis of Polyhydroxylated 2–Phenylbenzothiazoles and a Comparison of Their Cytotoxicities and Pharmacological Properties with Genistein and Quereetin", Stevens et al., J. Med. Chem, pp. 1689–1695, (1994), 37.

"Augmentation of IL–2 Activated Natural Killer Cell Adoptive Immunotherapy with Cyclophosphamide", Goldfarb et al., Anticancer Research 18, pp. 1441–1446, (1998).

*Primary Examiner*—Frederick Krass
*Attorney, Agent, or Firm*—Pillsbury Madison & Sutro LLP

[57] ABSTRACT

This invention pertains to methods of treating cancer by reducing tumor colony number in a mammalian host using benzothiazole activated natural killer cells and interleukin-2. The benzothiazoles are of the formula I:

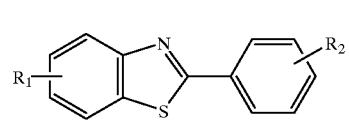

wherein $R_1$ is 4-OMe and $R_2$ is 4-tBu or 4-$CF_3$.

12 Claims, 4 Drawing Sheets

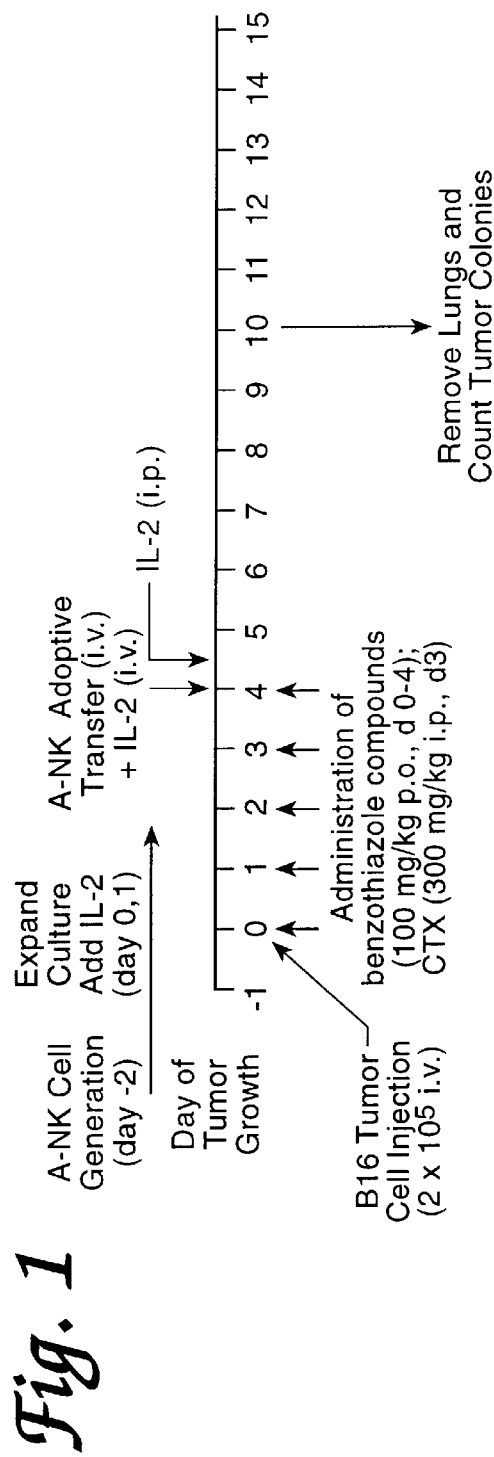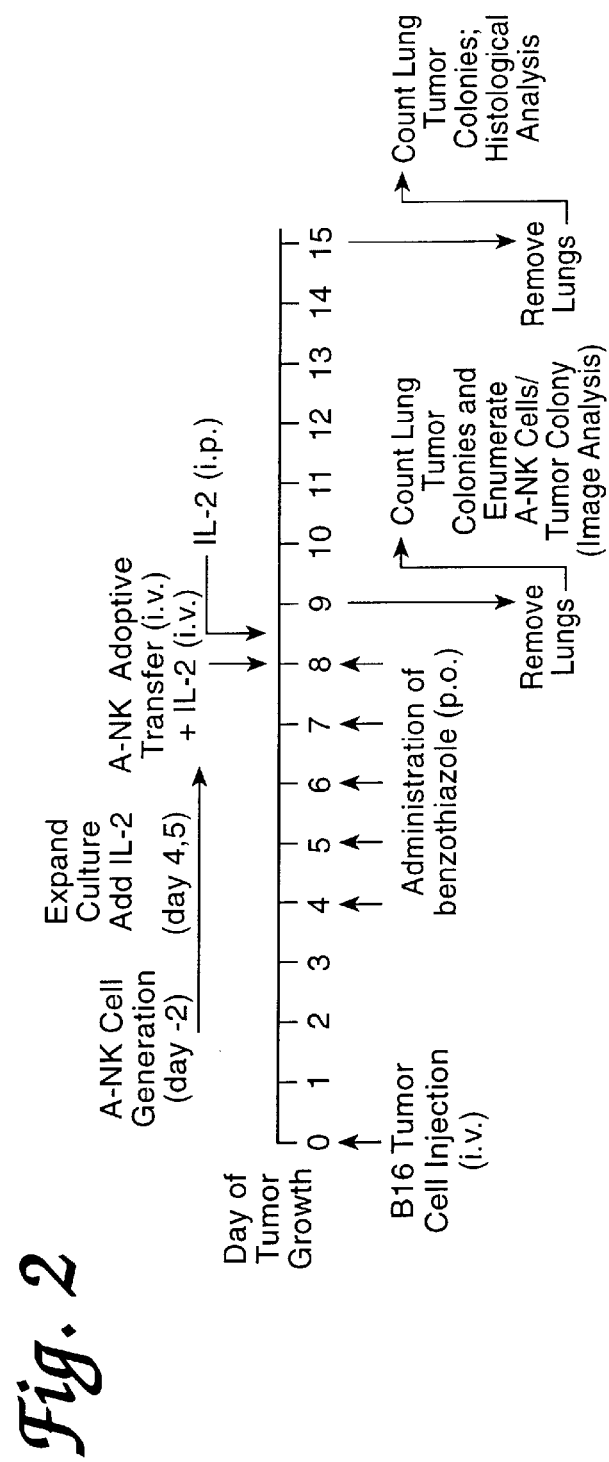

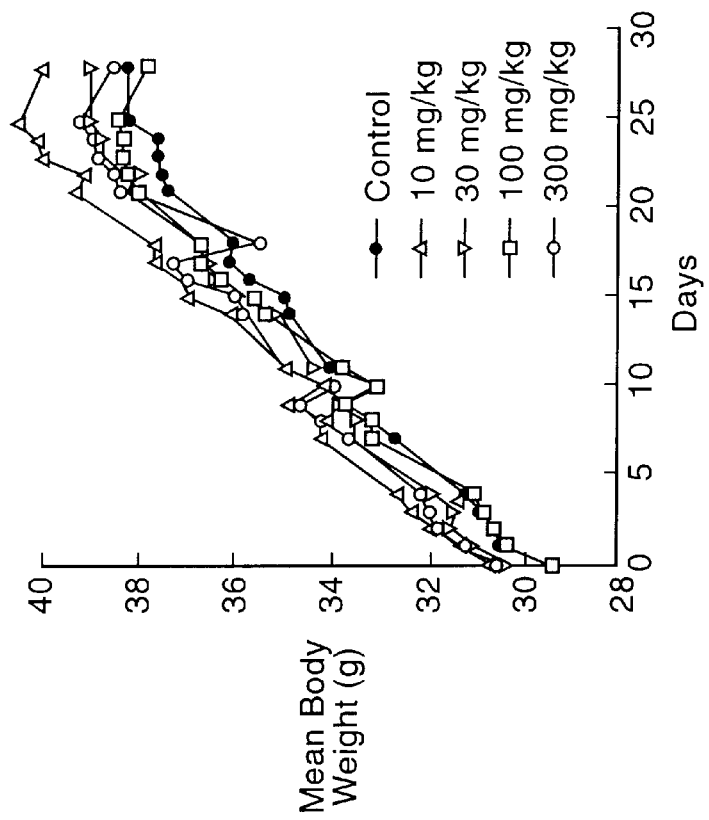
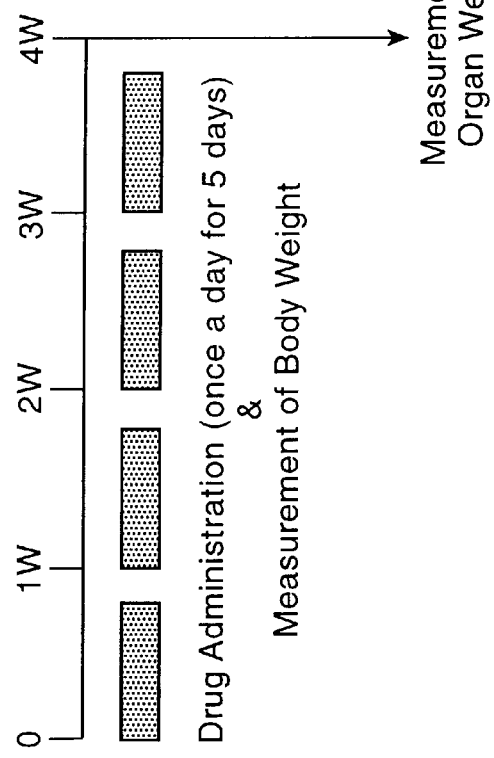
Fig. 5

METHODS OF REDUCING TUMOR COLONY NUMBER USING NOVEL BENZOTHIAZOLE COMPOUNDS

BACKGROUND OF THE INVENTION

1. Field of the Invention

This invention pertains to methods of treating cancer, and more particularly methods of reducing colony number using novel benzothiazole compounds in association with IL-2 (interleukin-2) activated natural killer (A-NK) cells and interleukin-2.

2. Description of Related Art

In the recent years there has been an ever increasing interest in the development and application of technologies for the treatment of cancer. However, the successful treatment of advanced cancer, i.e. cancer metastases has been mostly elusive.

It is recognized that patients with newly diagnosed solid malignancies already have occult, secondary metastatic tumors in distant organs. At least 50% of these metastases are resistant to conventional anti-cancer treatments of radiotherapy, chemotherapy or surgery and the majority of morbidity and mortality of patients with solid malignancies is great. This is directly related to the inability thus far to effectively treat cancer metastases.

According to Goldfarb and Whiteside, *Tumor Immunology and Cancer Therapy*, Pittsburgh Cancer Institute, Marcel Dekker, Inc. (1994), adoptive immunotherapy with interleukin-2 (IL-2) and lymphokine activated killer (LAK) cells or plastic adherence-enriched LAK (A-NK also known as A-LAK) cells has produced reductions in the number of metastatic lesions in several animal systems. In clinical settings, LAK cell therapy has also been at least successful in part, with complete or partial responses in 20–30% of the patients with advanced cancer, especially malignant melanoma and renal cell carcinoma. However, although adoptively transferred A-NK cells have the ability to find and infiltrate malignant lesions in a time dependent fashion, it is nonetheless a very inefficient process. Nevertheless, frequent long-term survival and complete eradication of metastases, has not yet been achieved, indicating the need for improvement of this therapeutic modality.

In a study by Basse et al., *Tissue Distribution of Adoptively Transferred Adherent LAK Cells: Role of the Route of Administration*, Nat. Immun. 11:193–202 (1992) it was reported that adoptive immunotherapy, in combination with IL-2 showed numerical reduction in the number of experimental metastases. However, it was also reported that complete remissions are seldom seen and that there is an urgent need to design new approaches to enhance the frequency and duration of the therapeutic responses.

Furthermore, according to Goldfarb, et al. *Preclinical studies of IL-2 Activated Natural Killer Effector Cells for Locoregional Therapy of Metastatic Cancer*, Journal of Infusional Chemotherapy, Vol. 4, No. 2 (1994), it was determined that IL-2 did not have a direct effect on cancer cells but mediated its antitumor activity by altering host immune responses, suggesting that immunologic therapy of cancer can be effective in selected patients with metastatic cancer. However, it was found that eradication of metastases with long-term survival has not been routinely achieved through this avenue.

There have been other approaches studied for treating cancer. One such approach is to transfect A-NK cells with genes for cytotoxic molecules to selectively target them to metastatic sites. However Goldfarb, *Natural Killer Cells and Gene Therapy: Potential of Gene Transfection for Optimizing Effector Cell Functions and for Targeting Gene Products into Tumor Metastases*, Nat Immun 13:131–140 (1994) indicated that additional knowledge is required concerning the potential role of specific cytokines in vivo for the therapy of established tumors.

Therefore, there is a present and urgent need for an anticancer agent that is more effective against highly invasive, advanced metastatic tumors which are resistant to conventional anti-cancer drugs. It is thus, an object of the present invention to provide an anticancer agent that is highly effective against very invasive, advanced metastatic tumors and that resolves the problems experienced with anticancer agents of the past. It is an object of the present invention to provide a method of treatment that reduces colony number.

SUMMARY OF THE INVENTION

The present invention is directed to a method of reducing tumor colony number in a mammalian host by administering to the mammalian host an effective amount of a benzothiazole compound having the formula I:

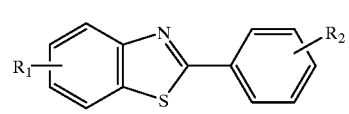

wherein $R_1$ is 4-OMe and $R_2$ is 4-tBu or 4-$CF_3$ in combination with effective amounts of interleukin-2 activated natural killer (A-NK) cells and interleukin-2. (IL-2 activated natural killer cells are also known as adherent lymphokine activated killer cells or A-LAK.)

The curing result in the host due to the method of the invention was found to be improved over the curing effect of interleukin-2 activated killer cells administered alone. Studies of the present compounds with A-NK cells and IL-2 have shown that the compounds of the invention enhance the capacity of A-NK cell and IL-2 to yield improved antimetastatic therapeutic efficacy under conditions where A-NK cell accumulation was not enhanced by itself. The compounds of the invention function to augment the antimetastatic therapeutic efficacy of adoptively transferred A-NK cells.

The amount of benzothiazole administered to the host is 10–300 mg/kg. The amount of interleukin-2 activated natural killer cells administered to the host is 3.0–4.0×$10^7$ cells, and the amount of interleukin-2 administered to the host is 240,000 IU.

BRIEF DESCRIPTION OF THE DRAWINGS

FIG. 1 is a flow diagram of experimental procedures for early B16 tumors, 4 day model;

FIG. 2 is a flow diagram of experimental procedures for late B16 tumors, 8 day model;

FIG. 5 is a graph of subacute toxicity of benzothiazole compound B, 4-methoxy-2-(4-trifluoromethylphenyl) benzothiazole in mice.

DETAILED DESCRIPTION OF THE INVENTION

Figure 3:
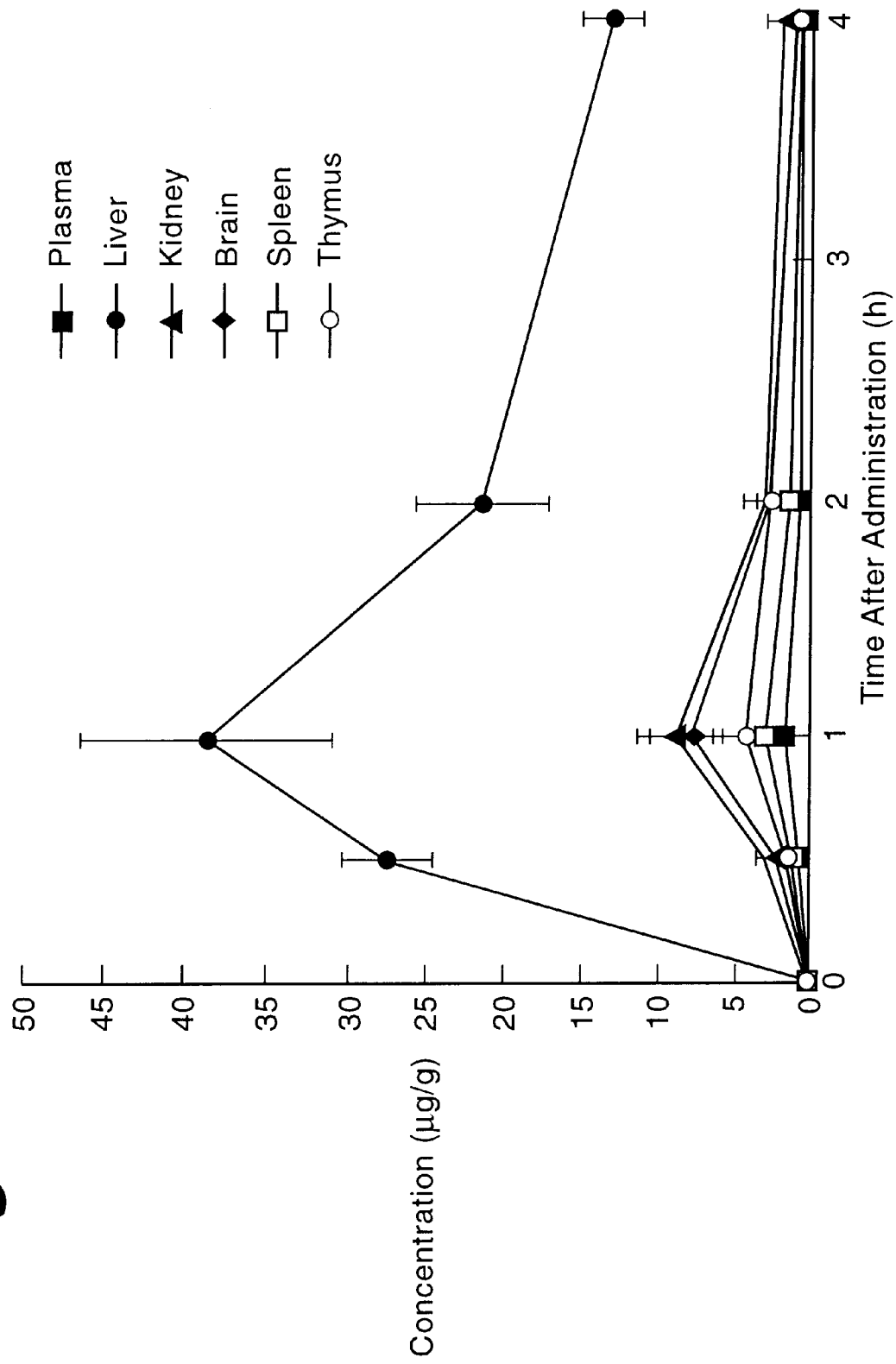
FIG. 3 is a graphic diagram of tissue distribution of benzothiazole compound B, 4-methoxy-2-(4-trifluoromethylphenyl)benzothiazole in mice.

The present invention is directed to a method of reducing tumor colony number in a mammalian host by administering to the mammalian host an effective amount of a benzothiazole compound having the formula I:

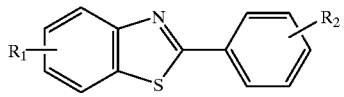

wherein $R_1$ is 4-OMe and $R_2$ is 4-tBu or 4-$CF_3$ in combination with effective amounts of interleukin-2 activated natural killer (A-NK) cells and interleukin-2. When $R_2$ is 4-tBu, the compound is referred to as compound A. When $R_2$ is 4-$CF_3$, the compound is referred to as compound B.

Method of preparing the benzothiazole compounds:

The general preparation of benzothiazole compounds such as those described herein above is set forth in U.S. Pat. No. 4,910,211 to Imamura et al., the entire disclosure of which is incorporated by reference. The method of obtaining the structural analogues used in the present invention, i.e. the $R_1$ and $R_2$ substituents for formula I are based on extension of the technology set forth in U.S. Pat. No. 4,910,211.

REFERENCE EXAMPLE 1

4-Methoxy-2-(4-trifluoromethyl phenyl) benzothiazole (Compound B):

1-(1) 4-Trifluoromethyl-2'-methoxybenzanilide

To a solution of 20.8 g of o-anisidine in 140 ml of pyridine was added dropwise a solution of 35.2 g of p-trifluoromethyl benzoyl chloride in 30 ml of tetrahydrofuran at 50° to 10° C. After stirring at room temperature for 1.7 hours, the reaction mixture was poured into 1.6 liters of water. The precipitate was collected by filtration, washed with water, and dried to give 48.9 g of 4- trifluoromethyl -2'-methoxybenzanilide.

(2) 4-Trifluoromethyl-2'-methoxybenzothioanilide

A mixture of 102.4 g of 4-trifluoromethyl-2'-methoxybenzanilide prepared by the same manner as described in (1), 77.2 g of Lawesson's reagent, and 400 ml of toluene was refluxed for 1 hour. The reaction mixture was cooled to about 100° C. and then 300 ml of water was added. The resulting mixture was refluxed for 1 hour. The organic layer was separated, dried over magnesium sulfate, and concentrated to about 200 ml of volume. The precipitate was collected by filtration, washed with toluene, and dried to give 86.2 g of 4-trifluoromethyl-2'-methoxybenzothioanilide.

A portion of this product was recrystallized from cyclohexane to give a product having a melting point of 118.5° to 119.5° C.

(3) 4-Methoxy-2-(4-trifluoromethyl phenyl)benzothiazole

To a solution of 50.8 g of potassium ferricyanide and 16.8 g of postassium hydroxide (purity≧86%) in 2 liters of water was added 20.0 g of 4-trifluoromethyl-2'-methoxybenzothioanilide obtained in (2) in small portions. The mixture was stirred at room temperature for 6 days. The precipitate was collected by filtration, washed with water, and dissolved in 150 ml of ethyl acetate. To this solution was added 150 ml of 10% HCl and the resulting mixture was stirred at room temperature for 3 hours. The organic layer was successively washed with water (x1), a saturated $NaHCO_3$ solution (x2) and brine (x1), dried over magnesium sulfate, and evaporated in vacuo. The residue was suspended in cyclohexane and stirred at room temperature for 2 hours. The precipitate was collected by filtration, washed with cyclohexane, and recrystallized twice from cyclohexane to give 9.7 g of 4-methoxy-2-(4-trifluoromethyl phenyl)-benzothiazole.

mp 104.5° C.

NMR (CDCl$_3$, δ ppm):4.10 (3H, s), 6.96 (1H, dd), 7.38 (1H,dd), 7.51 (1H, dd), 7.73 (2H, d), 8.23 (2H, d). Elemental analysis value (for $C_{15}H_{10}F_3NOS$) Calculated (%) C, 58.25; H, 3.26; N, 4.53. Found (%) C, 58.25; H, 3.25; N, 4.50.

REFERENCE EXAMPLE 2

4-Methoxy-2-(4-t-butylphenyl)benzothiazole (Compound A):

Compound A was prepared by the same manner as described in Reference Example 1.

mp 90.0–91.0° C. (n-hexane) NMR (CDCl$_3$, δ ppm):1.35 (9H,s),4.07(3H,s)6.91 (1H,dd),7.30(1H,dd),7.45–7.55(3H, m),8.00–8.10(2H,m). Elemental analysis value(for $C_{18}H_{19}NOS$) Calculated (%) C,72.69;H,6.44;N,4.71. Found (%) C,72.82;H6.47;N,4.69.

Method of preparing B16 melanoma cancer cells:

The B16 F1 melanoma model system, herein after referred to as B16 melanoma model system, is recognized as being highly resistant to treatment with many standard clinically used anti-cancer agents. Therefore, it was selected for testing because it is known to be reflective of the clinical situation for advanced melanoma.

Method of A-NK cell generation and expansion:

A-NK cells were prepared from mouse spleens. All procedures were carried out in a laminar flow hood using sterile reagents and equipment. Briefly, a single cell suspension was prepared by gently mashing the spleens through a 40 mesh stainless steel screen into complete media (CM) which consisted of RPMI 1640 supplemented with 10% heat-inactivated fetal bovine serum, 100 U/ml penicillin, 100 μg/ml streptomycin sulfate, 50 μg/ml gentamicin sulfate, 2 mM L-glutamine, $5\times10^{-5}$ M 2-mercaptoethanol and 1% MEM non-essential amino acids. The erythrocytes in the resulting suspension were lysed and the suspension was centrifuged and washed twice with CM. Splencytes were cultured in T-150 flasks at $1.5\times10^8$ per cells per flask (A flasks) in 50 ml of CM containing 6000 IU rhIL-2/ml. After 2 days the media and the non-adherent cells from the A flasks were transferred into new T-150 flasks (25 ml per flask—B flasks) and fresh CM+IL-2 (25 ml) was placed in the A flasks. The next day (day 3) the non-adherent cells and media from the B flasks were transferred to an equal number of T-150 C flasks and fresh CM+IL-2 was placed on the B flasks. On day 4 the media and the non-adherent cells from the C flasks were discarded and fresh CM+IL-2 to each flask. On day 6 the A-NK cells were harvested.

Effective amount of A-NK cells:

The effective amount of A-NK cells is $3-4\times10^7$ cells per 20 g mouse. This number of cells gives a maximal number of A-NK cells per metastasis while being insufficient to cause emboli due to clumping of the cells (Basse et al). The A-NK cells are administered intravenously to the mice.

Effective amount of IL-2:

IL-2 (obtained from Chiron corporation, Emeryville, Calif.) is administered at 120,000 IU i.v. per 20 g mouse initially and 120,000 IU i.p after 8 h. This amount of IL-2 was found to give maximal infiltration of tumors. Larger amounts although eliciting higher absolute numbers of A-NK cells per metastasis gave rise to unwanted side effects. In addition the increase in infiltration was not proportional to the increased amount of IL-2 administered.

Effective amount of benzothiazole:

Benzothiazoles were initially given at 100 mg/kg body weight p.o. (oral administration). This dose was well tolerated and increased doses to 300 mg/kg did not show any improvement in therapy. The dose of benzothiazole compound was mixed with 1% gum arabic diluent.

EXAMPLE 1

Method of administering benzothiazole compounds with IL-2 activated natural killer cells:

Referring to FIG. 1 which illustrated a flow diagram of procedures for tumor metastasis system, A-NK generation, therapy and analysis for arly B16 tumors used in the present invention. All experimental groups initially contained at least 7 animals. A-NK cell generation was started at day $-2$ and the culture was expanded on days 0 and 1 as described above.

Separately on day 0, B16 tumor cells ($2 \times 10^5$ i.v.) were injected into C57BL/6 mice. On days 0, 1, 2, 3 and 4, a benzothiazole compound of formula I (100 mg/kg, p.o.) was administered to the mice. On day 3 some animals received cyclophosphamide (300 mg/kg., i.p.) which is a standard chemotherapeutic drug.

On day 4, $3-4 \times 10^7$ A-NK cells plus 120,000 IU of IL-2 were adaptively transferred into tumor-bearing mice. Control mice received injections of vehicle diluent (1% gum arabic). After 8 h 120,000 IU of IL-2 was given to mice which had received A-NK cell injections and control mice received injections of vehicle. On day 10, the mice were sacrificed, their lungs removed and the rumor colonies counted.

EXAMPLE 2

Method of administering benzothizole compounds with IL-2 activated natural killer cells:

Referring to FIG. 2, which illustrates a flow diagram of experimental procedures for tumor metastasis system, A-NK generation and therapy and analysis of later B16 tumors used in the present invention. A-NK cell generation was started on day 2 and the culture was expanded as described above.

Separately on day 0, B16 tumor cells ($2 \times 10^5$ i.v.) were injected into C57BL/6 mice. On days 4,5,6,7 and 8, a benzothiazole compound of formula I (100 mg/kg, p.o.) was administered to the mice.

On day 8, $3-4 \times 10^7$ A-NK cells plus 120,000 IU of IL-2 were adaptively transferred into tumor-bearing mice. Control mice received injections of diluent vehicle (1% gum arabic). After 8 h 120,000 IU of IL-2 was given to mice which had received A-NK cell injections and control mice received injections of vehicle diluent. On day 9, the mice were sacrificed, their lungs removed and the tumor colonies counted.

Experimental results

With B16 melanoma cells administered on day 0 of A-NK cells administered on day 4, compound A [4-methoxy-2-(4-t-butylphenyl)benzothiazole] and compound B [4-methoxy-2-(4-trifluoromethylphenyl)benzothizole] enhanced the reduction B16 melanoma pulmonary metastases mediated by A-NK cell adoptive immunotherapy. As can be seen in Table 1, compound A in a combination with A-NK cells reduced the tumor burden by an average of 64% while A-NK cells alone reduced the tumor burden by only 24%. While the reduction in tumor burden obtained with A-NK cells alone was not statistically significant, the reduction observed using A-NK cells in combination with compound A was significant at the $p<0.005$ level in two experiments and at the $p<0.02$ level in one experiment. In these three experiments although cyclophosphamide reduced the tumor burden, it was only significant at the $p<0.05$ level in one. The results with compound B are given in Table 2. Significant reduction in tumor burden was seen in three separate experiments with significance at the $p<0.001$ level in one experiment; however, neither A-NK cells alone or cyclophosphamide yielded a significant reduction in tumor burden.

When A-NK cells were administered on day 9, the addition of compound A reduced the tumor burden on average by 38%, while A-NK cells alone reduced the tumor burden by only 19%. These two examples show that compounds A and B augment the anti-metastatic therapeutic effect of adoptively transferred A-NK cells.

Toxicity and pharmacokinetics

Figure 4:
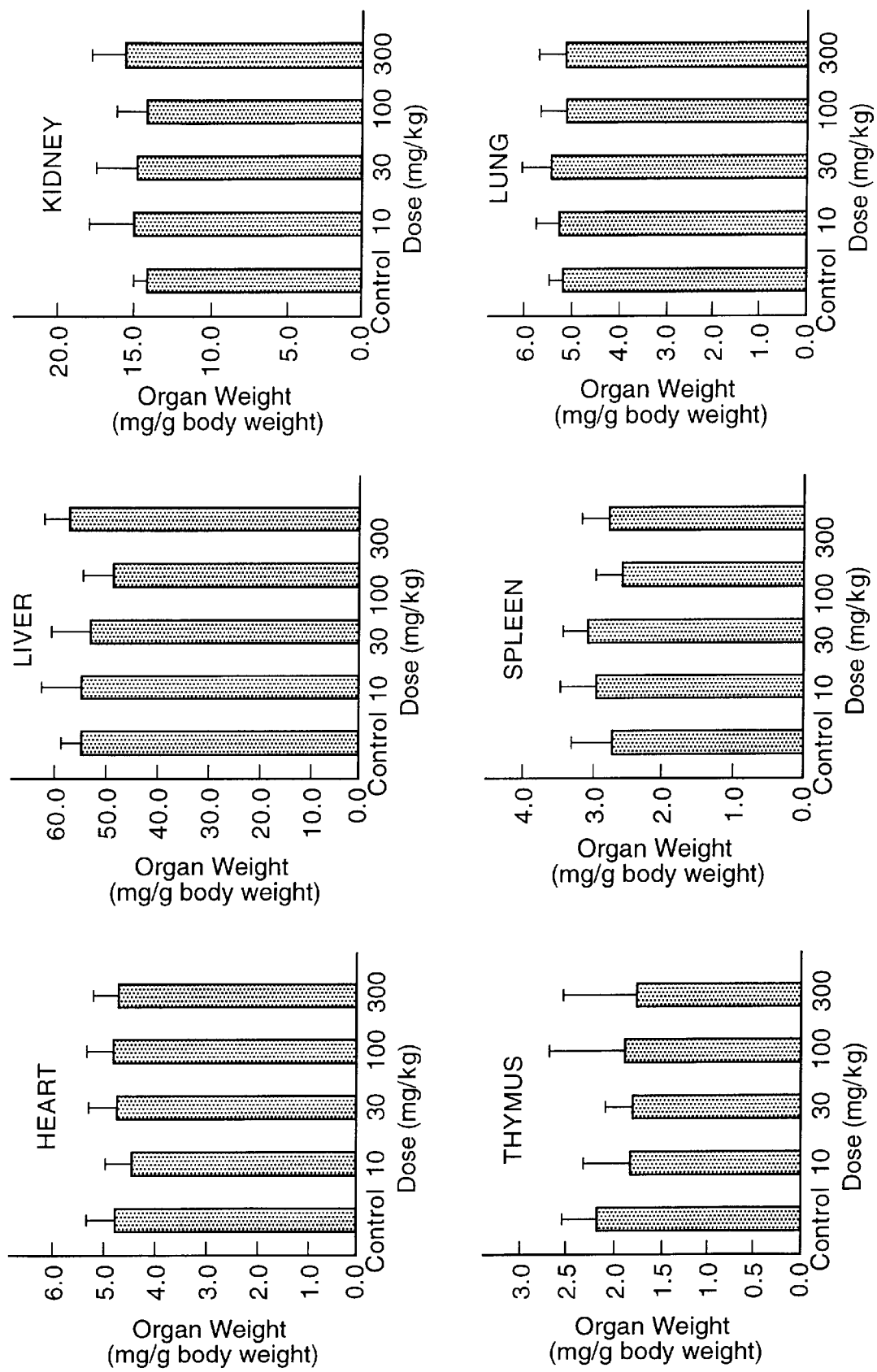
FIG. 4 is a series of graphs showing the effect of benzothiazole compound B, 4-methoxy-2-(4-trifluoromethylphenyl)benzothiazole on various organ weights in mice.

The compound B of the present invention has been tested for its pharmacokinetics and toxicity in mice. As shown in FIG. 3 peak levels of compound B occurred in the liver 1 h after p.o. administration of a single 100 mg/kg dose. FIG. 4 shows the protocol for a subacute toxicity study of compound B in mice. Mice were dosed for 5 consecutive days with 0–300 mg/kg of compound B in 1% gum arabic (p.o.). Their weight was measured in 1 week intervals and at 4 weeks the animals were sacrificed and their organ weights measured. There was no significant difference in either body weight change (FIG. 5) or organ weight change (FIG. 6) in the animals receiving compound B. These results indicate that the compounds used in the inventive method are safe and display excellent pharmacokinetics and pharmacodynamics.

From the above discussion, it can be seen that the method of the present invention of administering benzothiazole compounds with interleukin-2 activated natural killer cells and interleukin-2 exerts anti-metastatic therapeutic efficacy under conditions where interleukin-2 activated natural killer cells themselves or compounds themselves or conventional anti-cancer drugs are ineffective and fail to yield significant anti-metastatic therapy.

The complete disclosure of all articles and papers cited herein are incorporated herein by reference. The scope of this invention is not limited by the foregoing description and examples.

TABLE 1

Summary of Efficacy of Compound A in Day 4 B16 Model

| | Number of Pulmonary Metastases (± standard deviation) | | |
|---|---|---|---|
| Experiment # | Control | A-NK Cells | Compound A + A-NK Cells | Cyclophosphamide |
| 1 | 59 ± 41 | 40 ± 28 | 24 ± 19* | 33 ± 25 |
| 2 | 32 ± 22 | 36 ± 17 | 13 ± 7* | 18 ± 12 |
| 3 | 222 ± 74 | 106 ± 69 | 58 ± 35** | 81 ± 60* |

*p < 0.05 vs. control using Student's t-test (one-tail)
**p < 0.02 vs. control using Student's t-test (one-tail)

TABLE 2

Summary of Efficacy of Compound B in Day 4 B16 Model

| Experiment # | Control | A-NK Cells | Compound B + A-NK Cells | Cyclophosphamide |
|---|---|---|---|---|
| | | Number of Pulmonary Metastases (± standard deviation) | | |
| 1 | 125 ± 66 | 117 ± 63 | 66 ± 39* | 135 ± 55 |
| 2 | 187 ± 114 | 179 ± 69 | 88 ± 49* | 156 ± 120 |
| 3 | 199 ± 45 | 156 ± 96 | 88 ± 60** | 272 ± 110 |

*$p < 0.05$ vs. control using Student's t-test (one-tail)
**$p < 0.001$ vs. control using Students's t-test (one-tail)

What is claimed is:

1. A method for reducing tumor colony number in a mammalian host in need thereof comprising administering to the mammalian host an effective amount of a benzothiazole having the following formula I:

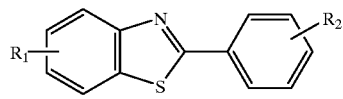

wherein $R_1$ 4-OMe, and $R_2$ is 4-tBu or 4-$CF_3$ in combination with effective amounts of interleukin-2 activated natural killer cells and interleukin 2.

2. The method of claim 1, wherein $R_2$ is 4-tBu.

3. The method of claim 1, wherein $R_2$ is 4-$CF_3$.

4. The method of claim 1, wherein the administering of the benzothiazole compound comprises oral administration.

5. The method of claim 1, wherein the administering of the interleukin-2 activated killer cells and interleukin 2 comprises intravenous administration.

6. The method of claim 1, wherein the mammalian host is a mouse.

7. The method of claim 1, wherein the tumor is a melanoma.

8. The method of claim 1, wherein the mammalian host bears advanced cancer with established metastases.

9. The method of claim 1, wherein the amount of benzothiazole administered is between about 10–300 mg/kg.

10. The method of claim 1, wherein the amount of interleukin-2 activated natural killer cells administered is between about 3–4×10$^7$ cells and the amount of interleukin 2 administered is about 240,000 IU.

11. The method of claim 1, wherein the amount of benzothiazole administered is between about 10–300 mg/kg, the amount of interleukin-2 activated natural killer cells administered is between about 3–4×10$^7$ cells and the amount of interleukin 2 administered is about 240,000 IU.

12. The method of claim 1, wherein the benzothiazole is administered along with a pharmaceutically acceptable carrier.

* * * * *